United States Patent

Olesen et al.

Patent Number: 5,158,969
Date of Patent: Oct. 27, 1992

[54] INDOLE DERIVATIVES AS POTASSIUM CHANNEL BLOCKERS

[75] Inventors: Soren-Peter Olesen, Brønshøj; Leif H. Jensen, Copenhagen; Peter Moldt, Humlebaek, all of Denmark; Mikkel Thaning, Hjärup, Sweden

[73] Assignee: NeuroSearch A/S, Glostrup, Denmark

[21] Appl. No.: 748,050

[22] Filed: Aug. 21, 1991

[51] Int. Cl.$^5$ ............................................. A61K 31/40
[52] U.S. Cl. .................................................... 514/419
[58] Field of Search ......................................... 514/419

Primary Examiner—S. J. Friedman
Attorney, Agent, or Firm—Gordon W. Hueschen

[57] ABSTRACT

A method of treating a disease in a mammal, including a human, responsive to blockade of potassium channels, which comprises administering to a mammal in need thereof an effective amount of a compound having the formula

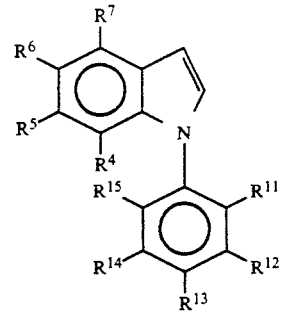

wherein
$R^{11}$, $R^{12}$, $R^{13}$, $R^{14}$ and $R^{15}$ independently of each other are hydrogen, $CF_3$, $NO_2$, $NH_2$, OH, $C_{1-6}$-alkyl, $C_{1-6}$-alkoxy or phenyl; and
$R^4$, $R^5$, $R^6$ and $R^7$ independently of each other are hydrogen, halogen, $CF_3$, $C_{1-6}$-alkyl, $NO_2$, $NH_2$, OH or $C_{1-6}$-alkoxy,
and a method as above wherein 1-(4-methoxyphenyl)-indole is employed,
and a method as above wherein depression, memory disorders, Alzheimers disease and diabetes 2 is treated,
and further a method as above wherein the active ingredient is administered in the form of a pharmaceutical composition thereof, in which it is present together with a pharmaceutically-acceptable carrier or diluent.

8 Claims, No Drawings

INDOLE DERIVATIVES AS POTASSIUM CHANNEL BLOCKERS

The present invention relates to a novel treatment with indole derivatives.

OBJECT OF THE INVENTION

It is an object of the present invention to provide a novel method of treatment of diseases in mammals, including a human, responsive to blockade of potassium channels which comprises administering to a mammal in need thereof an indole derivative.

BACKGROUND OF THE INVENTION

It is generally well known that blockade of potassium ($K^+$) channels of $\beta$-cells of mammals, including a human, will stimulate the insulin release of the $\beta$-cells thus offering an alternative way of treating diabetes 2 symptoms in mammals.

Further it is generally well known that blockade of potassium ($K^+$) channels leads to a depolarization and excitation of living cells. However, until now, no pharmaceutical utility of compounds possessing such activity has been demonstrated although there would be a scientific rationale to suggest that such compounds might have a potential in the treatment of depression and Alzheimer's disease. Such rationale is based upon the fact that a cell excitant probably would stimulate an unspecific release of transmitter substances like serotonin, dopamine and acetylcholine for example.

SUMMARY OF THE INVENTION

The invention then, inter alia, comprises the following, alone or in combination:

A method of treating a disease in a mammal, including a human, responsive to blockade of potassium channels, which comprises administering to a mammal in need thereof an effective amount of a compound having the formula

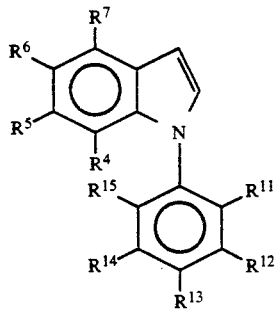

wherein
$R^{11}$, $R^{12}$, $R^{13}$, $R^{14}$ and $R^{15}$ independently of each other are hydrogen, $CF_3$, $NO_2$, $NH_2$, OH, $C_{1-6}$-alkyl, $C_{1-6}$-alkoxy or phenyl; and $R^4$, $R^5$, $R^6$ and $R^7$ independently of each other are hydrogen, halogen, $CF_3$, $C_{1-6}$-alkyl, $NO_2$, $NH_2$, OH or $C_{1-6}$-alkoxy, and a method as above wherein 1-(4-methoxyphenyl)-indole is employed, and a method as above wherein depression, memory disorders, Alzheimers disease and diabetes 2 is treated, and further a method as above wherein the active ingredient is administered in the form of a pharmaceutical composition thereof, in which it is present together with a pharmaceutically-acceptable carrier or diluent.

BIOLOGICAL ACTIVITY

The compounds provided for the novel treatment of the present invention are potent blockers of the high conductance calcium activated $K^+$-channel, sometimes referred to as the Big $K^+$ channel or the $BK_{Ca}$ channel. The $BK_{Ca}$ channel is present in most neuronal cells, in airway and vascular smooth muscle cells as well as in pancreatic $\beta$-cells.

The ability of the compounds for the novel treatment of the present invention, to block the $BK_{Ca}$ channel can be demonstrated in several ways.

All electrophysiological experiments were performed with patch-clamp technique (Hamill et al., Pflügers Arch. 391, 85-100 (1981). The ion composition of the internal solution was (in mM) 4 NaCl, 140 KCl, 1 $CaCl_2$, 1 $MgCl_2$, 2 EGTA, 10 HEPES and the external solution contained 140 NaCl, 4 Kcl, 2 $CaCl_2$, 1 $MgCl_2$ and 10 HEPES.

SINGLE CHANNEL EXPERIMENTS

In inside-out patches of bovine aortic smooth muscle cells in which the $BK_{Ca}$ channel is the predominant $K^+$ channel for example 1-(4-methoxyphenyl)-indole potently at 20 $\mu$M blocked the $BK_{Ca}$ channel.

Likewise in pancreatic $\beta$-cells the same compound potently blocked the $BK_{Ca}$ channel.

PHARMACOLOGICAL STUDIES 1-(4-methoxyphenyl)-indole has been studied in the socalled tail suspension test as described by L. Steru et al., Prog. Neuro-Psychopharmacol. Biol. Psychiatry 11, 659-671 (1987).

Female NMRI mice (20-25 g, 10 mice per dose) were suspended by the tail with adhesive tape for 6 min. The mice alternated between phases of activity (trying to escape) and immobility (despair). The duration of immobility was recorded manually. Saline, 1-(4-methoxyphenyl)-indole or desipramine were administered i.p. 30 min before the start of the test.

Saline treated mice were immobile approximately half the time during the experiment. Desipramine, a standard anti-depressive compound, reduced the immobility dose-dependently at doses between 1 and 30 mg/kg i.p. At doses between 10 and 100 mg/kg i.p. 1-(4-methoxyphenyl)-indole inhibited the immobility dose-dependently. Both antidepressive drugs and psychostimulants decrease the immobility in this test.

To demonstrate the memory enhancing effects of the compounds provided for the novel treatment of the present invention the social recognition model described by Dantzer et al., Psychopharmacology, 91, 363-368 (1987) has been used. In short, adult male Wistar rats (350 g) were housed individually in normal transparent plexiglas cages. After a habituation period of at least 24 hours a juvenile male Wistar rat (25-30 days old) was introduced in the cage in a 5 min period (first exposure). A second exposure of the same juvenile rat for another 5 min period was performed either 5 min later or 120 min later. In one case, another juvenile rat was introduced 120 min after an exposure of a juvenile rat. The adult rat was administered either saline or different doses of 1-(4-methoxyphenyl)-indole i.p. 15 min before the first exposure of the juvenile rat.

In both sessions (1st and 2nd exposure period) the total duration of investigatory behaviour consisting of sniffing, nosing and grooming performed by the adult rat was noted.

The adult rat (n=10-20) used generally 100-110 sec investigating the juvenile rat on the first exposure. With a 5 min delay the adult rat used only in average 62 sec on investigatory behaviour (p<0.001, paired Student's t-test) on the second exposure of the same juvenile rat, while no significant difference in duration of investigatory behaviour was seen with a 120 min delay. This shows that a short lasting (<2 hours) social recognition memory exist using this paradigm. The memory seems basically to be based on recognition of urine odour.

Treatment with 1-(4-methoxyphenyl)-indole (7.5-30 mg/kg i.p.) did not interfere with the adult rats investigatory behaviour on the first exposure, however, on the second exposure of the same juvenile rat 120 min later a significant decrease in investigatory behaviour was seen. If the second exposure (after treatment with 1-(4-methoxyphenyl)-indole 30 mg/kg i.p. 15 min before the first exposure) was performed with a new (unknown) juvenile rat normal investigatory behaviour was seen, indicating that the effects of 1-(4-methoxyphenyl)indole are not due to unspecific effects like sedation, lack of motivation, loss of smell, toxic effects etc. Taken together these results indicate that the compounds enhance the memory processes involved in social recognition.

CHEMISTRY

The chemistry and chemical synthesis of the indole derivatives provided for the novel treatment of the present invention is well documented.

Derivatives not specifically disclosed in the literature may be easily synthesized according to well known procedures, for example according to the Ullman procedure:

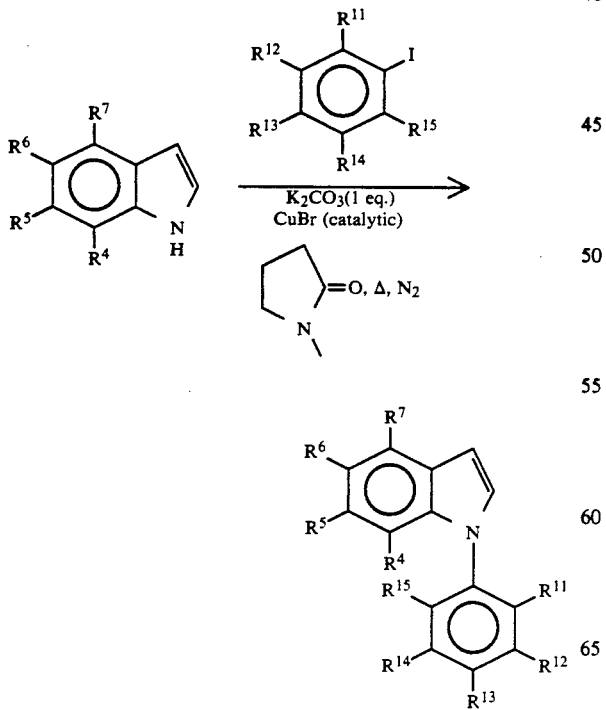

PHARMACEUTICAL COMPOSITIONS

The compounds provided for the novel treatment of the invention, together with a conventional adjuvant, carrier, or diluent, may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed. Tablets containing ten (10) milligrams of active ingredients or, more broadly, 0.1 to one hundred (100) milligrams, per tablet, are accordingly suitable representative unit dosage forms.

METHOD OF TREATING

The indole derivatives disclosed herewith are extremely useful in the treatment of disorders of mammals due to their potent potassium channel blocking properties. These properties make the compounds extremely useful in the treatment of depression, memory disorders, Alzheimer's disease and diabetes 2 as well as other disorders responsive to potassium channel blocking activity. The compounds provided for the novel treatment of the present invention may accordingly be administered to a subject, including a human, in need of treatment alleviation, or elimination of an indication associated with the potassium channels. This includes especially depression, memory disorders, Alzheimer's disease and diabetes 2.

Suitable dosage ranges are 0.1-1000 milligrams daily, 10-500 milligrams daily, and especially 30-100 milligrams daily, dependent as usual upon the exact mode of administration, form in which administered, the indication toward which the administration is directed, the subject involved and the body weight of the subject involved, and further the preference and experience of the physician or veterinarian in charge.

We claim:

1. A method of treating a disease in a mammal, including a human, responsive to blockade of potassium channels, which comprises administering to a mammal in need thereof an effective amount of a compound having the formula

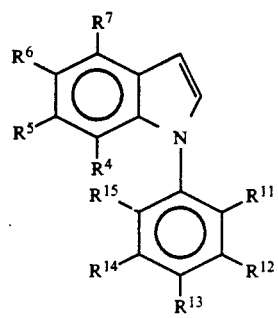

wherein $R^{11}$, $R^{12}$, $R^{13}$, $R^{14}$, and $R^{15}$ independently of each other are hydrogen, $CF_3$, $NO_2$, $NH_2$, OH, $C_{1-6}$-alkyl, $C_{1-6}$-alkoxy or phenyl; and $R^4$, $R^5$, $R^6$, and $R^7$ independently of each other are hydrogen, halogen, $CF_3$, $C_{1-6}$-alkyl, $NO_2$, $NH_2$, OH or $C_{1-6}$-alkoxy.

2. A method as in claim 1 wherein depression, memory disorders, Alzheimers disease and diabetes 2 is treated.

3. A method as in claim 1 wherein the active ingredient is administered in the form of a pharmaceutical composition thereof, in which it is present together with a pharmaceutically-acceptable carrier or diluent.

4. A method as in claim 2 wherein the active ingredient is administered in the form of a pharmaceutical composition thereof, in which it is present together with a pharmaceutically-acceptable carrier or diluent.

5. A method as in claim 1, wherein the compound employed is 1-(4-methoxyphenyl)-indole.

6. A method as in claim 2, wherein the compound employed is 1-(4-methoxyphenyl)-indole.

7. A method as in claim 3, wherein the compound employed is 1-(4-methoxyphenyl)-indole.

8. A method as in claim 4, wherein the compound employed is 1-(4-methoxyphenyl)-indole.

* * * * *